United States Patent [19]

Kozulic

[11] Patent Number: 5,202,007
[45] Date of Patent: Apr. 13, 1993

[54] HYDROPHILIC SYNTHETIC GELS AND THEIR USE IN ELECTROPHORESIS

[76] Inventor: Branko Kozulic, Georg Kempfstrasse 7, 8046 Zurich, Switzerland

[21] Appl. No.: 696,696

[22] Filed: May 7, 1991

Related U.S. Application Data

[63] Continuation-in-part of Ser. No. 688,752, Apr. 22, 1991, Pat. No. 5,185,466, and Ser. No. 293,840, Jan. 5, 1989, abandoned.

[30] Foreign Application Priority Data

Apr. 20, 1990 [GB] United Kingdom ............... 9008873

[51] Int. Cl.$^5$ .................. G01N 27/26; G01N 27/447; B01D 57/02
[52] U.S. Cl. ............................. 204/182.8; 204/299 R; 204/180.1
[58] Field of Search ............. 204/299 R, 182.8, 182.9, 204/180.1

[56] References Cited

U.S. PATENT DOCUMENTS 4,925,545  5/1990  Murel ............................... 204/182.9

OTHER PUBLICATIONS

Mirjana Kozulic, Branko Kozulic, and Klaus Mosbach "Poly-N-acryloyl-Tris Gels as Anticonvection Media for Electrophoresis and Isoelectric Focusing" Analytical Biochemistry 163 (1987) 506–512.
Branko Kozulic, Klaus Mosbach, and Maciej Pietrzak "Electrophoresis of DNA Restriction Fragments in Poly-N-Acryloyl-Tris Gels" Analytical Biochemistry 170 (1988) 478–484.

*Primary Examiner*—John Niebling
*Assistant Examiner*—John S. Starsiak, Jr.
*Attorney, Agent, or Firm*—Nikaido Marmelstein Murray & Oram

[57] ABSTRACT

An electrophoretic method of resolving mixtures of molecules by putting the molecules in an ionic form; contracting them with a porous gel made up of a polymer comprising units derived from a monomer of the formula:

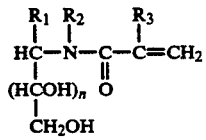

wherein
  $R_1$ is H, $CH_2OH$ or $(CHOH)_m CH_2OH$, m being 1 or 2;
  $R_2$ is H, a monohydroxyalkyl radical, a polyhydroxyalkyl radical or a hydrocarbon radical; and
  n is an integer of 1–4;
imposing electrophoretic conditions on said gel;
migrating the different molecules different distances in said gel;
and thereby separating said different molecules.

18 Claims, 4 Drawing Sheets

HYDROPHILIC SYNTHETIC GELS AND THEIR USE IN ELECTROPHORESIS

This application is a continuation-in-part of application Ser. No. 293,840 filed Jan. 5, 1989, now abandoned and 688,752 filed on Apr. 22, 1991 now U.S. Pat. No. 5,185,466 the entire contents of both of which are incorporated.

FIELD OF THE INVENTION

This invention concerns gels comprising hydrophilic acrylic monomers and the use of these gels for electrophoretic separation of molecules.

BACKGROUND OF THE INVENTION

Purification and analysis of molecules is very often carried out by forcing these molecules to migrate through a gel. In gel electrophoresis the driving force is a voltage gradient across the gel and the gel matrix comprises natural or synthetic polymers. The synthetic polymers are usually formed by polymerization of double bonds present in monomer and cross-linker molecules. The monomers currently in use are of the amide type and they include acrylamide, N-acryloyl-tris(hydroxymethyl)aminomethane (NAT) (references 1-3) and N-acryloyl morpholine (reference 4). The gels made of the last two monomers have been recently introduced. The most important features of poly(NAT) gels are pronounced hydrophilicity and a higher porosity compared to polyacrylamide gels. The higher porosity of poly(NAT) gels could be advantageously used for separation of larger molecules by electrophoresis and isoelectric focusing (references 1-3). It appeared worth searching for a monomer which will produce even more porous gel, since such a gel would be beneficial in many applications, including isoelectric focusing, multiphasic zone electrophoresis and electrophoresis of proteins, lipoproteins, proteoglycans and nucleic acids. As a working hypothesis it was assumed that NAT yields gels of higher porosity because its molecular weight is higher than that of acrylamide. Thus, an NAT solution has a molar concentration lower than the acrylamide solution of the same percentage. After polymerization the lower molar concentration of the NAT solution presumable results in fewer polymer chains per unit volume, leading to gels of increased porosity. The finding (reference 1) that a poly(NAT) gradient gel exhibited a porosity approximately three-fold higher than porosity of the corresponding polyacrylamide gel, in accordance with the 2.5 fold lower molarity, lend support to the above assumption. If this simple assumption is correct, then even more porous gels will be formed from monomers of higher molecular weight. In addition to size of a monomer, other factors can influence porosity of a gel. Thus, if interactions exist between monomer molecules, or between a monomer and a growing polymer, or between the growing polymer chains, then as a result of these interaction the polymer chains may not be randomly distributed. If they form some kind of bundles, larger pores will be created. In addition to a higher molecular weight, the new monomers should fulfill at least two further requirements. First, they should be hydrophilic in order to give homogenous aqueous gels. Second, the double bond of these monomers should efficiently polymerize under rather mild conditions used for the preparation of gels for electrophoresis. From the above assumptions and considerations, it appeared that gels with desirable properties may be formed of monomers derived from amino sugar alcohols, as described below by the formula:

where
$R_1$ is H, $CH_2OH$ or $(CHOH)_m CH_2OH$, m being 1 or 2;
$R_2$ is H or $CH_3$;
$R_3$ is H or $CH_3$; and
n is an integer of 1-4;

These monomers are hydrophilic as they contain at least three hydroxyl groups. Further, due to adjacent amide group the double bond in the monomers is expectedly more reactive than a typical double bond.

Two of the monomers represented by the above formula, N-acryloyl-1-amino-1-deoxy-D-glucitol and N-methacryloyl-1-amino-1-deoxy-D-glucitol as well as their linear polymers are known (reference 5 and 6). However, in the two references no data were reported concerning polymerization of either of the two monomers in the presence of a cross-linker to form an aqueous gel. Moreover, there was no indication as to whether such an aqueous gel may represent a matrix suitable for electrophoretic separation of molecules.

The monomers of the above formula include compounds with the nitrogen atom linked to a carbon atom having one or two hydrogens as well as the compounds in which hydrogen from the amide nitrogen is substituted by methyl group. In the two known monomers, N-acryloyl-1-amino-1-deoxy-D-glucitol and N-methacryloyl-1-amino-1-deoxy-D-glucitol, the nitrogen is linked to a carbon atom with two hydrogens. The attempts to synthesize other monomers of the formula above by the process described in reference 5 failed. We have initially used sugar precursors readily available, that is N-acetyl-2-amino-2-deoxy-D-glucose and N-methyl-1-amino-1-deoxy-D-glucitol. However, neither N-acryloyl-2-amino-2-deoxy-D-glucitol, a compound with the nitrogen atom linked to carbon with one hydrogen, nor N-methyl-N-acryloyl-1-amino-1-deoxy-D-glucitol, a compound with methyl group on the nitrogen, crystallized from the water-ethanol-ether solution of reference 5. After modification of the preparation process, as described in detail in reference 7, all monomers of the general formula could be obtained. The modified process includes treatment of the reaction mixture with an anionic and a cationic ion exchanger to remove the remaining reactants and formed by-products. Further, the water solution of the monomer is evaporated at atmospheric pressure. Those monomers which dried out to give a solid residue were recrystallized and those remaining as a viscous liquid were directly used for preparation of gels.

As shown in reference 7, the new monomers could be polymerized in presence of a cross-linker to give water insoluble gels. It was shown that such a gel is a matrix suitable for isoelectric focusing and therefore also for other electrophoretic techniques, since it is well known that requirements imposed on a matrix for isoelectric focusing are more stringent than those for other electrophoretic techniques. For example, agarose needs to be modified in a special way before it is suitable for preparation of isoelectric focusing gels (references 8 and 9).

Gels made of the monomers of the general formula are suitable for electrophoresis, as demonstrated by experimental results of reference 7 in accordance with the assumptions discussed above. However, it is not apparent whether there may be important differences in properties of gels made of various monomers of the general formula. Thus, if molecular weight of the monomer determines porosity of the gel, then gels prepared from equal amounts of monomers having identical molecular weight should exhibit equal porosity. In that case, the gels made for example of N-acryloyl-1-amino-1-deoxy-D-glucitol,N-acryloyl-2-amino-2-deoxy-D-glucitol and N-acryloyl-1-amino-1-deoxy-D-galacitol will be equally porous. On the other hand, if gel formation differs from one monomer to the other because the polymerization rate of each monomer is unique or if polymer interactions are different, then the resulting porosity will not be equal. Since our current knowledge on porosity of synthetic gels is based on only three monomers, that is acrylamide, NAT and N-acryloyl morpholine, which are structurally more different than the monomers of this invention, it was not possible to make predictions about porosity of gels made of structurally related monomers including isomers.

Electrophoretic migration of molecules in polyacrylamide gels is mostly described in terms of the extended Ogston model (references 10 and 11). Accordingly, the measured mobility, $\mu$, can be related to the free mobility, $\mu_o$, of a migrating molecule with radius R, as well as to the gel percentage T, total length of the gel fibers, $l'$, and the fiber radius, $r$:

$$\log \mu = \log \mu_o - \pi l'(r+R)^2 T \times 10^{-16}$$

or $$\log \mu = \log \mu_o - K_r T$$

where the retardation coefficient, $K_r$, is defined as $$K_r = \pi l'(r+R)^2 \times 10^{-16}$$

The extended Ogston model has been extensively used to analyze electrophoretic migration of various macromolecules in polyacrylamide gels, mainly in order to enable estimation of the molecular weight and radius of an unknown molecule. However, since the retardation coefficient is correlated also to the length of gel fibers and their radius, this model can be used as an approach for characterization of different gels. After analysis of gels made of the monomers shown by the general formula above according to the extended Ogston model, it was surprisingly found that gel properties vary significantly from one gel to the another, as described in this invention.

SUMMARY OF THE INVENTION

This invention is based on the finding that polymers and cross-linked polymers of at least one monomer having the following formula:

wherein:
$R_1$ is H, $CH_2OH$, $(CHOH)_m CH_2OH$ and m is 1 or 2;
$R_2$ is H, a monohydroxy alkyl, a polyhydroxy alkyl or a hydrocarbon radical, preferably of 1 to about 30 carbon atoms;
$R_3$ is H or $CH_3$; and
n is an integer of 1-4;
are well suited to use in electrophoretic processes. The preferred polymers according to this invention are those made from monomers in which $R_2$ is hydrogen or a methyl group.

Suitable cross-linkers for use in combination with these monomers are those which have polymerizable olefinic unsaturation. Exemplary of these materials are N,N'-methylene-bis-acrylamide, N,N'-methylene-bis-methacrylamide, ethylene diacrylate, ethylene dimethacrylate, N,N'(1,2, dihydroxyethylene)bisacrylamide, N,N'-diallyltartardiamide, N,N',N''-triallylcitric triamide, poly(ethylene)glycol diacrylate, N,N'-bisacryloyl cystamine and olefinic agarose.

It is also considered to be within the scope of this invention to copolymerize the above-described monomers with one or more co-monomers, in addition to or instead of the above mentioned cross-linkers. These co-monomers are exemplified by acrylamide, N-acryloyl tris (hydroxymethyl)aminomethane, N-acryloyl morpholine, methacrylamide, methyl methacrylate, methyl acrylate, 1,2-dihydroxypropyl methacrylate, glycidyl methacrylate and 4-vinylphenyl glucopyranoside.

The electrophoretic method of this invention is carried out by contacting a porous gel of a suitable polymer, as described, with an ionic species of a group of molecules to be separated, or a single or group of molecules to be characterized; imposing electrophoretic conditions on the gel; and thus causing the ionic species to migrate in the porous gel. The migration distance is a function of the inherent nature of the molecules and the molecules can therefor be characterized by the extent of this migration. Sains and/or detectors of known character can be used to assist in this characterization. A mixture of closely related molecules can be separated in this manner.

DETAILED DESCRIPTION OF THE INVENTION

The present invention will hereinbelow be described in further detail with reference to the accompanying drawings, in which.

The composition of synthetic gels for electrophoresis is usually described in terms of T and C, where T represents gel concentration in percentage (g/100 ml) and C degree of cross-linking (g cross-linker)×100 divided by (g monomer+g cross-linker). It is generally assumed that the gel concentration corresponds to the sum of the monomer and cross-linker quantity taken for polymerization, but this is not always the case because the polymerization reaction is seldom quantitative. The electrophoretic migration of molecules in gels depends on both T and C. When gels of different T are analyzed according to the extended Ogston model, it is necessary to keep C constant (reference 10 and 11). The gels can be polymerized in different shapes, such as sheets or rods. It is more convenient to make rod-shaped gels when a large number of gels needs to be analyzed, since smaller amounts of monomers are required and a larger number of gels can be run at the same time.

The extended Ogston model has been used to describe the electrophoretic migration of nucleic acids and proteins. Proteins are run under native or denaturing conditions. Electrophoresis of proteins under native conditions gives more information about the molecular properties of that protein. However, a large number of gels is needed since only one protein is usually run in one gel to avoid ambiguities concerning band identification. On the other hand, band identification is simple after denaturation of proteins with sodium dodecyl sulfate (SDS), because then all proteins have essentially equal charge to mass ratio and therefore smaller proteins migrate faster. Five SDS denatured proteins have been used for evaluation of gels of the present invention. They include myosin (MW 200 000), beta-galactosidase (MW 116 000), phosphorylase b (MW 97 000), bovine serum albumin (MW 67 000) and ovalbumin (MW 45 000).

The gels were polymerized in glass tubes 4 mm in diameter. The length of gels was from 75 to 80 mm and their concentration was varied from 5 to 10%. The degree of cross-linking was 3% and N,N'-methylene-bis-acrylamide (Bis) was used as the cross-linker. Electrophoresis was carried out at 80 V in 60 mM Tris-acetate buffer pH 8.0, containing 1.5 mM sodium EDTA and 0.1% SDS. The position of bromphenol blue tracking dye in the gel was marked by inserting a piece of 0.2 mm thick wire in the middle of the band. After staining and destaining, the band distances were measured with a ruler. The measured values were used to construct three different graphs. First, migration distances from each gel were plotted against the log of MW. Second, the log of migration distances were plotted against the gel concentration (Ferguson plot). The $K_r$ values determined from the Ferguson plot were used to construct the R-plot, from which gel fiber length and radius were estimated.

Figure 1:
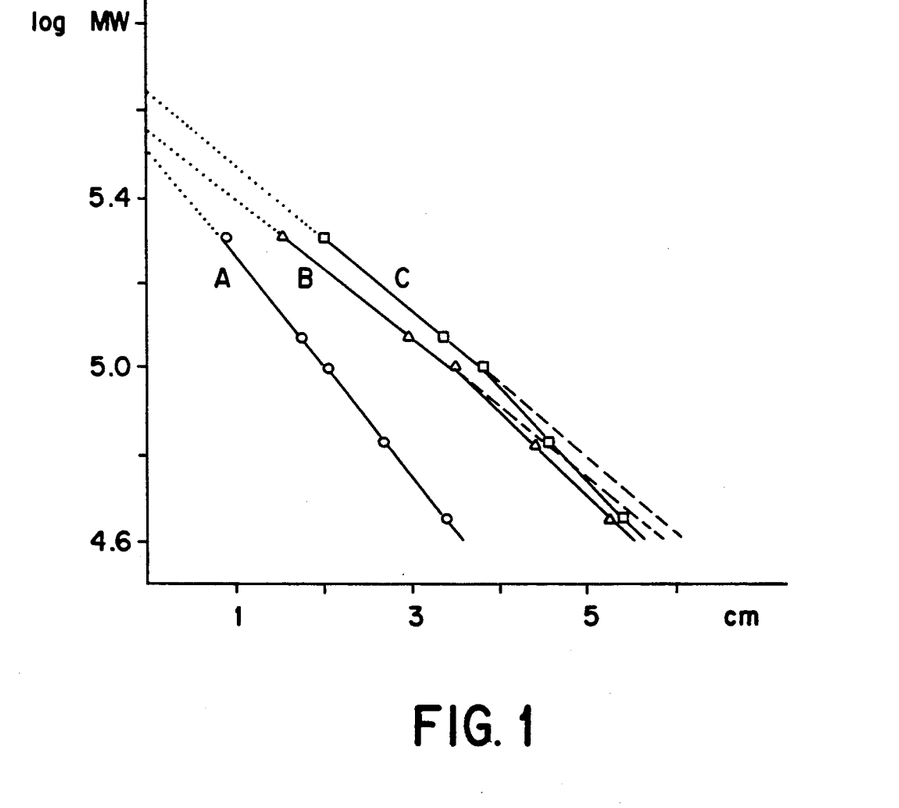
FIG. 1 is a graphical presentation of relationship between migration distance and log molecular weight of five proteins in a 6% polyacrylamide (curve A), 6% poly(NAT) (curve B) and 6% poly(N-acryloyl-1-amino-1-deoxy-D-glucitol) (curve C) gel.

In characterization of the gels of this invention, polyacrylamide gels are used as an internal standard since they have been characterized in detail by the extended Ogston model. Poly(NAT) gels are also included for comparison. A typical graph showing the relationship between migration distance and log MW is shown in FIG. 1. Curve A relates to 6% polyacrylamide gel, curve B to 6% poly(NAT) gel and curve C to 6% poly(N-acryloyl-1-amino-1-deoxy-D-glucitol) gel. All proteins migrated further in the poly(N-acryloyl-1-amino-1-deoxy-D-glucitol) gel than in the other two gels. Further, the points indicate essentially a straight line in A, whereas a broken line fits better the points in B and C. Better description of the relationship between log MW and distance by a broken line is even more pronounced at 5 and 5.5% gel concentration (not shown). On contrary, at gel concentration of 7% and higher the points fitted essentially a straight line. Similar results were obtained with gels made by polymerization of N-acryloyl-1-amino-1-deoxy-D-galactitol,N-acryloyl-2-amino-2-deoxy-D-glucitol,N-acryloyl-N-methyl-1-amino-1-deoxy-D-glucitol and N-acryloyl-N-methyl-1-amino-1-deoxy-D-galacitol. When the broken line of FIG. 1 is extended downwards (dashed line), the result indicates that bovine serum albumin and ovalbumin migrate slower than expected. This finding can be explained by assuming that at the low gel concentrations the sieving becomes so small that the mobility of these proteins approaches $\mu_o$, which is then equal for all SDS-protein complexes. By extension of the lines of FIG. 1 upwards (dotted line) it is possible to estimate the exclusion limit of the gels, assuming that the relationship at high MW would remain linear. Thus, the exclusion limit, calculated by taking antilogarithms of the values on the ordinate, of the polyacrylamide gel is 330, poly(NAT) gel 360 and poly(N-acryloyl-1-amino-1-deoxy-D-glucitol) gel 450 000. The other four gels gave the exclusion limit from 350 to 630 000.

Figure 2:
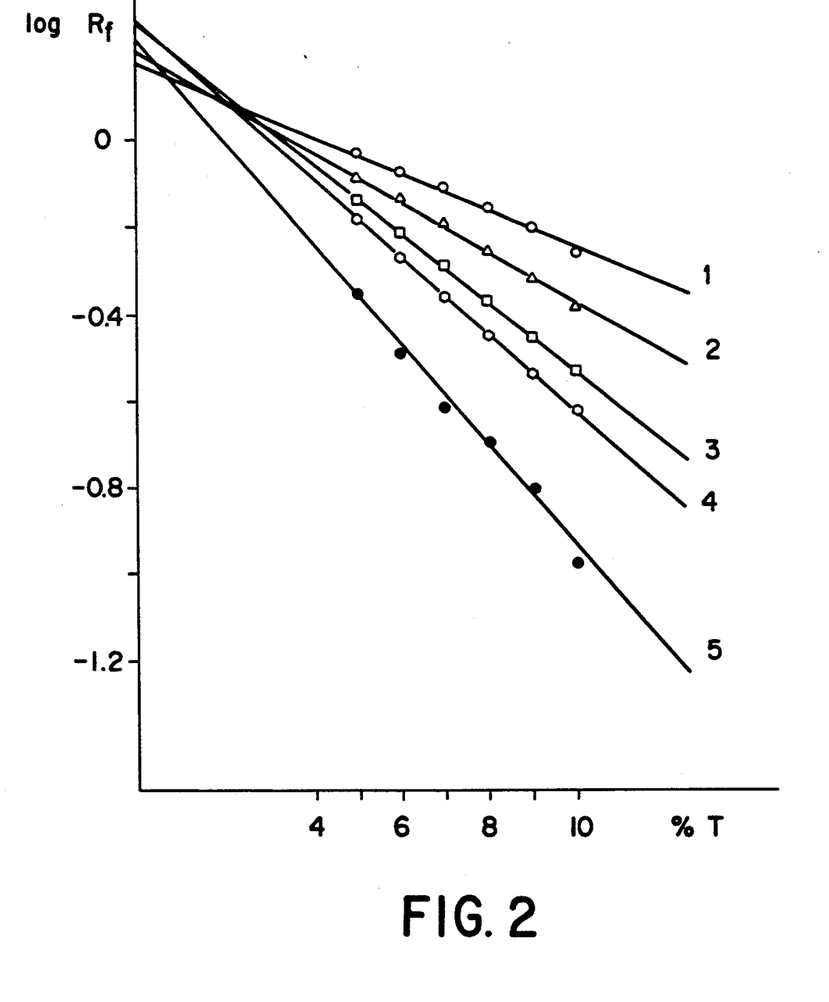
FIG. 2 is a graphical presentation of the relationship between log migration distance and gel concentration (Ferguson plot) of five proteins in 5, 6, 7, 8, 9 and 10% poly(N-acryloyl-1-amino-1-deoxy-D-glucitol) gels. The proteins include: 1-ovalbumin (MW 45 000), 2-bovine serum albumin (MW 67 000), 3-phosphorylase b (MW 97 000), 4-beta-galactosidase (MW 116 000) and 5-myosin (MW 200 000)

FIG. 2 shows the Ferguson plot describing the relationship between log migration distance and gel concentration for 5-10% poly(N-acryloyl-1-amino-1-deoxy-D-glucitol) gels. Ferguson plots similar to that of FIG. 2 were obtained for four other monomers of this invention as well as for polyacrylamide and poly(NAT) gels. Generally, the points fitted well the straight lines, except those representing myosin at high gel concentrations (9 and 10%) and sometimes ovalbumin and bovine serum albumin at lower (5 and 6%) gel concentrations. A curved line would have better fitted those points, but in order to enable estimation of the retardation coefficients a straight line was drawn through the points representing lower gel concentrations. The lines intersected in roughly one point which was at 0 or up to 2.5% gel concentration, depending on the gel. In theory, all lines should intersect in one point at 0 gel concentration, since all SDS-protein complexes have essentially equal free electrophoretic mobility. The possible reasons explaining why in practice the lines may intersect at different points are discussed in reference 11. The retardation coefficients, corresponding to slopes of the straight lines in FIG. 2, were calculated for all proteins in all gels. The $K_r$ values of the examined proteins were the highest in polyacrylamide gel, followed by poly(NAT) gel and then by gels made of monomers of this invention. The only exception was poly(N-acryloyl-2-amino-2-deoxy-D-glucitol) gel in which the $K_r$ values of some proteins were higher. It is noted that the retardation coefficients were calculated from $R_f$ values rather than from absolute mobilities. Therefore the values depend on migration distances of the tracking dye and protein. All proteins migrated a longer distance in the gels of this invention than in a polyacrylamide gel of the same gel concentration, confirming higher porosity of the new gels. It is noteworthy that the use of absolute mobilities to calculate the $K_r$ values and construct the R-plot gave less reproducible results.

Figure 3:
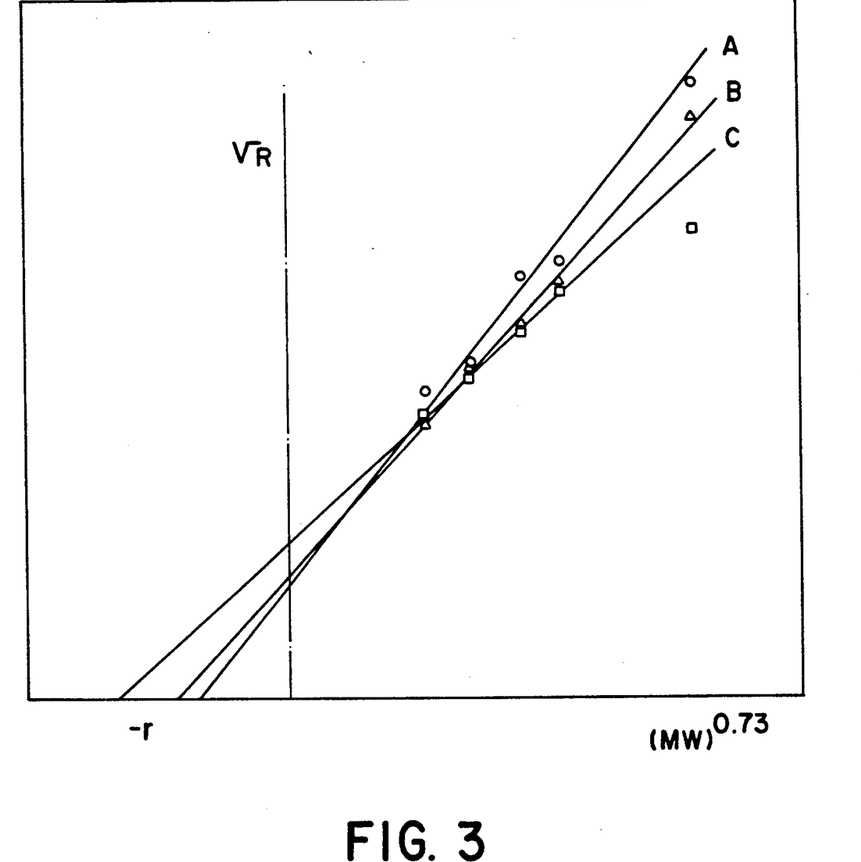
FIG. 3 represents an R-plot showing the relationship between retardation coefficients, estimated from the Ferguson plots, and molecular radius, calculated from the molecular weight, of the five proteins. Curve A relates to polyacrylamide, curve B to poly(NAT) and curve C to poly(N-acryloyl-1-amino-1-deoxy-D-glucitol) gel. The intercept on the abscissa correlates to gel fiber radius.

In R-plots (FIG. 3) the square root of retardation coefficients is plotted against the radius of proteins. The radius of native proteins or protein-SDS complexes can be used (reference 12). The radius of a protein-SDS-complex may be correlated to MW by equation $R = k(MW)^{0.73}$ (reference 13). Here the constant k was arbitrary chosen as 1. The straight line A represents polyacrylamide gel, line B poly(NAT) and line C poly(N-acryloyl-1-amino-1-deoxy-D-glucitol) gel. Similar plots were obtained for gels made of N-acryloyl-1-amino-1-deoxy-D-galactitol, N-acryloyl-2-amino-2-deoxy-D-glucitol, N-acryloyl-N-methyl-1-amino-1-deoxy-D-glucitolandN-acryloyl-N-methyl-1-amino-1-deoxy-D-galactitol. According to the extended Ogston model, in R-plot the intersection of the straight line on abscissa corresponds to -r, that is the radius of the gel fiber. The intersection on the ordinate relates to the square root of the fiber volume ($V_f$, in ml per gram polymer dry weight), and slope of the straight line relates to the square root of the total fiber length (l', in cm/g). Table 1 summarizes the values estimated for the five gels. Since the major goal of this evaluation was to compare different gels, all values are given relative to polyacrylamide gel. It is apparent that all gels have a fiber radius larger than polyacrylamide gel. Further, fiber volumes of the new gels are bigger but the fiber lengths are smaller than in polyacrylamide gel. There are clear differences among gels made of different monomers. For example, N-acryloyl-N-methyl-1-amino-1-deoxy-D-galactitol gel has l' and $V_f$ values more similar to that of poly(NAT) gel than to other monomers. In addition, fiber volume of N-acryloyl-1-amino-1-deoxy-D-galactitol is almost twice as high as the fiber volume of the corresponding N-methyl derivative. Most significant are differences in the total fiber length among the new gels. The values vary from 0.29 to 0.97 relative to polyacrylamide.

The retardation coefficient depends on the fiber radius and total fiber length:

$$K_r = \pi l'(r+R)^2 \times 10^{-16}$$

Clearly, the increase in the fiber radius decreases porosity, since the $K_r$ increases. Thus if the l' of the new gels and acrylamide were equal, the higher radius of the gels of this invention would make them less porous. However, the found l' values are lower and although the fiber radii are larger, the retardation coefficients of proteins in the new gels are generally smaller, because a retardation coefficient is more sensitive to changes in l' than in r for large molecules, as shown by the equation above. It can be assumed that the fiber radius is higher in the new gels because size of the side chains in each repeating unit is larger. However, it is not clear why the total fiber length is smaller. It is possible that the polymer chains are shorter because the molar monomer concentration before polymerization is lower, but this is at best only a partial explanation since gels made of monomers of the same size, and therefore molar concentration, have widely different l' (Table 1).

TABLE 1

The fiber radius r, fiber volume $V_F$, and fiber length l' of gels comprising different monomers as estimated from the R-plots. The values for acrylamide gel were taken as 1.

| Monomer | r | $V_F$ | l' |
|---|---|---|---|
| Acrylamide | 1 | 1 | 1 |
| NAT | 1.1 | 1.2 | 0.84 |
| N-acryloyl-1-amino-1-deoxy-D-glucitol | 1.8 | 2.2 | 0.56 |
| N-acryloyl-2-amino-2-deoxy-D-glucitol | 1.7 | 2.5 | 0.86 |
| N-acryloyl-1-amino-1-deoxy-D-galactitol | 2.3 | 2.6 | 0.53 |
| N-acryloyl-N-methyl-1-amino-1-deoxy-D-glucitol | 2.9 | 2.0 | 0.29 |
| N-acryloyl-N-methyl-1-amino-1-deoxy-D-galactitol | 1.3 | 1.4 | 0.97 |

TABLE 2

The migration distances of ovalbumin and myosin measured in gels (T = 6, C = 3%) comprising different monomers and N,N'-methylene-bis-acrylamide.

| Monomer | Migration distance as % of the gel length | | Percentage of the gel length occupied by the five proteins |
|---|---|---|---|
| | ovalbumin | myosin | |
| Acrylamide | 45 | 9 | 35 |
| NAT | 64 | 19 | 46 |
| N-acryloyl-1-amino-1-deoxy-D-glucitol | 65 | 25 | 38 |
| N-acryloyl-2-amino-2-deoxy-D-glucitol | 64 | 16 | 49 |
| N-acryloyl-1-amino-1-deoxy-D-galactitol | 61 | 21 | 40 |
| N-acryloyl-N-methyl-1-amino-1-deoxy-D-glucitol | 69 | 35 | 34 |
| N-acryloyl-N-methyl-1-amino-1-deoxy-D-galactitol | 65 | 19 | 45 |

As shown above, the extended Ogston model is suitable for comparative evaluation of different gels. The comparison of gels can also be done by measuring the migration distance of a protein in various gels under identical electrophoresis conditions or by estimation of the gel length occupies by proteins of a certain size range. A comparison of migration distances in 6% gels is given in Table 2. The results indicate significant differences among the gels of this invention as well as between them and the polyacrylamide gel. For example, myosin migrated further in gels comprising N-acryloyl-N-methyl-1-amino-1-deoxy-D-glucitol and N-acryloyl-1-amino-1-deoxy-D-glucitol than in the corresponding galactitol gels. The same protein migrated in all gels considerably further than in the polyacrylamide gel. The gel length occupied by proteins was significantly different in different gels. Accordingly, the separation selectivity differs from one gel to another. Thus in practice, when it is desirable to have the 45-200 000 MW proteins spread as much as possible across the gel, then N-acryloyl-N-methyl-1-amino-1-deoxy-D-galactitol gel is preferable. When all protein molecules need to migrate to the bottom of the gel, for detection or collection, other gels, for example N-acryloyl-N-methyl-1-amino-1-deoxy-D-glucitolandN-acryloyl-1-amino-1-deoxy-D-glucitol gels are better suited. The results also show that different gel concentrations are needed for optimal resolution of proteins having different MW. As expected, lower gel concentrations are better for separation of larger proteins and higher gel concentrations for smaller proteins.

Of interest to the present invention is the observation that some gels swell more than the others during staining and destaining. For example, gels made of N-acryloyl-1-amino-1-deoxy-D-galactitol changed their length only negligible, whereas gels made of N-acryloyl-N-methyl-1-amino-1-deoxy-D-glucitol swelled about 30% over their original size (6% gel). Further, after staining the gels with Coomassie Brillant Blue R-250, some of them destained much faster than the others. For example, gels made of N-acryloyl-1-amino-1-deoxy-D-galactitol and N-acryloyl-1-amino-1-deoxy-D-glucitol destained faster than the gels made of acrylamide, N-acryloyl-N-methyl-1-amino-1-deoxy-D-galactitol or NAT. It is noteworthy that N-acryloyl-N-methyl-1-amino-1-deoxy-D-glucitol destained faster than N-acryloyl-N-methyl-1-amino-1-deoxy-D-galactitol, although they are isomers. In practice, therefore, some gels of the present invention are advantageous also because less time is needed for complete destaining of the gels after electrophoresis.

Separation of proteins according to their isoelectric point has been carried out in a poly(N-acryloyl-2-amino-2-deoxy-D-glucitol) gel (reference 7). When N-acryloyl-N-methyl-1-amino-1-deoxy-D-galactitol and N-acryloyl-1-amino-1-deoxy-D-glucitol were used to prepare gels for isoelectric focusing, a similar band pattern of sharp bands was obtained. The gels were polymerized on a plastic support and the carrier ampholytes were introduced into the gels after polymerization, that is the gels were first polymerized, washed in distilled water and dried. The dried gels were then reswollen in an ampholyte solution. It is noted that the dried gels including N-acryloyl-N-methyl-1-amino-1-deoxy-D-galactitol curled more than gels of the same percentage and degree of cross-linking including N-acryloyl-1-amino-1-deoxy-D-glucitol.

The gels of the present invention were evaluated also for electrophoretic separation of DNA. Properties of a gel are known to depend not only on the total gel concentration but also on the degree of cross-linking and the nature of the cross-linker. For evaluation of the new gels according to the extended Ogston model it was necessary to keep constant the degree of cross-linking and to use always the same cross-linker, as noted above. However, for a more complete illustration of the present invention it was important to assess also the influence of the cross-linking degree and cross-linker type on gel properties and electrophoretic separation. Thus, gels comprising three different cross-linkers were used for electrophoresis of nucleic acids. They include N,N'-methylene-bis-acrylamide (Bis), piperazine-di-acrylamide (PDA) and Acryl Aide ™ (FMC Corporation). The cross-linkers differ among themselves in several properties. Accordingly, Bis and PDA are both of the acrylamide type, but the distance of the two double bonds in PDA is larger than that in Bis. Further, the PDA molecule is expectedly more rigid and the amide nitrogens do not contain a hydrogen atom as in Bis. The Acryl Aide ™ cross-linker is profoundly different, because it is an olefinic agarose derivative (reference 14). Thus in contrast to Bis and PDA, the double bonds are not of the acrylamide type, the cross-linker is polymeric and therefore it contains many double bonds in one molecule. In addition, distances between double bonds are variable as are the number of double bonds in individual agarose chains and the lengths of the agarose chains.

Many different gel combinations comprising various monomers and cross-linkers were prepared and used for electrophoresis of DNA, as described in more detail in the Examples. It is noteworthy that the gel appearance depended strongly not only on degree of cross-linking but also on type of the cross-linker. For example, the gel comprising N-acryloyl-N-methyl-1-amino-1-deoxy-D-galactitol and Bis (T=6%, C=3%) was very slightly opaque, whereas the gel of the same T and C but comprising PDA instead of Bis was strongly opaque and brittle. Although transparent or slightly opaque gels are mostly used for electrophoresis, in some applications strongly opaque gels have been found advantageous (reference 15).

DNA molecules varying in size from 75 to about 20 000 bp have been electrophoresed in the gels of this invention. The gel concentrations were mostly from 5 to 10% and the gels were run in the submerged electrophoresis mode. The concentration of buffer in the gel was different from the concentration of the running buffer, due to reasons outlined in reference 16. Electrophoresis was carried out in an improved submerged gel apparatus described in reference 17. The resolution of DNA molecules was dependent on the gel concentration, degree of cross-linking, type of cross-linker and the running conditions. For example, in N-acryloyl-N-methyl-1-amino-1-deoxy-D-galactitol-Bis gel (T=6, C=3) after electrophoresis for 2 h and 15 min at 7 V/cm the 123 bp fragment was about 1 cm distant from the gel bottom and at least 14 bands were distinguishable in the 123 bp ladder. In the 1 kbp ladder, the 75 bp fragment migrated out of the gel and all fragments from 134 to 5090 bp were fully resolved. In the corresponding gel with T=10 and C=3 run for 4 h at 7 V/cm, the 123 bp fragment was about 2 cm away from the gel bottom and only 10 bands were clearly distinguishable in the 123 bp ladder. However, distances between adjacent bands in the size range from 100 to 600 bp were much larger, indicating that this gel is advantageous for separation of DNA fragments within that range. The migration distances and resolution were dependent also on degree of cross-linking, as determined in N-acryloyl-N-methyl-1-amino-1-deoxy-D-galactitol-Bis gels having constant T (6%) but differing in C (2.0, 2.2, 2.4, 2.6, 2.8 and 3.0%). Thus, the 123 bp fragment migrated about 0.5 cm further in the C=2.0 than in the C=3.0 gel, but the resolution of 201 and 220 bp bands from the 1 kbp ladder was better in the latter gel. In gels made of other monomers including N-acryloyl-1-amino-1-deoxy-D-galactitol, N-acryloyl-2-amino-2-deoxy-D-glucitol, N-acryloyl-N-methyl-1-amino-1-deoxy-D-glucitol and N-acryloyl-1-amino-1-deoxy-D-glucitol and N-acryloyl-1-amino-1-deoxy-D-xylitol, the resolution was comparable to that obtained in the N-acryloyl-N-methyl-1-amino-1-deoxy-D-galactitol gel. Only with the N-acryloyl-2-amino-2-deoxy-D-glucitol-Bis gel some problems were encountered during electrophoresis in the submarine mode, because the gel was only loosely attached to the plastic support and partially detached after about one hour. The migration distances were different from one gel to another, in line with differences in $K_r$ estimated above. For example, under identical conditions all DNA fragments migrated further in N-acryloyl-N-methyl-1-amino-1-deoxy-D-glucitol and N-acryloyl-1-amino-1-deoxy-D-glucitol than in N-acryloyl-N-methyl-1-amino-1-deoxy-D- galactitol gel of the same gel concentration and degree of cross-linking.

The gels were mostly prepared from monomer crystals dissolved in an appropriate buffer. However, as noted above some monomers of the general formula remained as viscous solutions which resisted all crystallization attempts. One example of such a monomer is N-acryloyl-1-amino-1-deoxy-D-xylitol. Nevertheless, this monomer was successfully used for separation of DNA from 100 to 4000 bp and the resolution and band sharpness were equally good as in other gels.

The electric field strength is known to significantly affect the resolution of nucleic acid fragments larger than 1 kbp. To improve the resolution, 5 and 6% poly(N-acryloyl-N-methyl-1-amino-1-deoxy-D-galactitol) and 6% poly(N-acryloyl-1-amino-1-deoxy-D-glucitol) gels were run at 2 V/cm for 24 h. DNA fragments larger than 2 kbp from the lambda/Hind III digest were resolved in all gels. In the 5% poly(N-acryloyl-N-methyl-1-amino-1-deoxy-D-galactitol) gel the bands migrated considerably further than in the 6% gel, but they were also more diffuse.

The type of cross-linker has a strong influence on resolution of DNA molecules in the gels of this invention. Thus, the DNA bands were less sharp and resolution was worse in the N-acryloyl-N-methyl-1-amino-1-deoxy-D-galactitol-PDA gel (T=6%, C=2%) than in the corresponding gel cross-linked with Bis. The effect was even more pronounced at C=3%. On contrary, the gel comprising N-acryloyl-N-methyl-1-amino-1-deoxy-D-galactitol and Acryl Aide (T=6, C=2%) showed only slightly inferior resolution in the lower size range compared to the gel cross-linked with Bis. In Acryl Aide cross-linked gel the cluster of high MW bands from the 1 kbp ladder migrated about 0.5 cm further than in gels cross-linked with the other two cross-linkers. The good resolution achieved in the gel cross-linked with Acryl Aide indicated that the monomers readily polymerize with other compounds having suitable double bonds. This property enables formation of composite gels. As expected, two monomers of the general formula could be co-polymerized. Thus, a gel (T=6%, C=3%) comprising equal amounts of N-acryloyl-N-methyl-1-amino-1-deoxy-D-galactitol and N-acryloyl-1-amino-1-deoxy-D-glucitol was copolymerized with Bis and used for DNA electrophoresis. Further, another gel (T=6, C=3%) comprising equal amounts of N-acryloyl-N-methyl-1-amino-1-deoxy-D-galactitol and acrylamide was copolymerized with Bis for analysis of DNA fragments. There was only a minor difference of DNA pattern in the first gel compared to the DNA pattern seen in gels containing only one of the two monomers. However, all DNA fragments migrated a much shorter distance in the second composite gel and the resolution of DNA fragments above 1 kbp was rather poor. Moreover, a composite gel (T=6%, C=3%) was prepared which contained one monomer but two different cross-linkers. It included N-acryloyl-N-methyl-1-amino-1-deoxy-D-galactitol cross-linked with Bis and PDA (weight ratio 2:1). In this gel the bands were less sharp than in the corresponding gel containing only Bis. The composite gels described above always contained a cross-linker. However, it is noted that agarose composite gels with or without covalently cross-linked polyacrylamide or even only linear polymers have been used for electrophoretic separation of molecules (references 18-20).

In accordance with conventional techniques the gels of the present invention have been polymerized in the form of sheets or rods and used for electrophoresis at the electric field strength from 2 to 10 V/cm. There exists, however, a novel electrophoretic technique wherein the gels are polymerized inside a thin long capillary having an internal diameter of 50 to 200 μm and the electrophoretic runs are carried out at over 100 V/cm (reference 21). The gels of this invention have been polymerized in 100 μm capillaries and used for electrophoresis. The remarkable resolution of DNA fragments achieved (FIG. 4) shows that the gels of this invention can be advantageously used for separation of ionic species by capillary gel electrophoresis. Due to distinctive properties of gels of this invention, an optimal gel can be chosen depending on a particular separation goal. For example, when it is desirable to have maximal selectivity then poly(N-acryloyl-N-methyl-1-amino-1-deoxy-D-galactitol) is suitable, but when a short analysis time is more important then gels made of poly(N-acryloyl-1-amino-1-deoxy-D-glucitol) are better.

Thus, in the practice of the principles of the present invention it is possible to make many different aqueous gels and advantageously use them for electrophoretic separation of molecules. To more fully describe the structure and uses of the present invention, the following exemplifications, not intended as limitations unless otherwise specifically indicated herein, are included.

EXAMPLE 1

SDS Electrophoresis of Proteins in poly(N-acryloyl-1-amino-1-deoxy-D-glucitol), poly(NAT) and polyacrylamide Gels N-acryloyl-1-amino-1-deoxy-D-glucitol (0.97 g), recrystallized from ethanol, and N,N'-methylene-bisacrylamide (0.03 g) were dissolved in 60 mM Tris-30 mM acetic acid buffer pH 8.0, containing 1.5 mM disodium EDTA and 0.1% SDS. The volume was adjusted to 10 ml to give a stock solution. The stock solution was diluted in microcentrifuge tubes to produce 1 ml of 5, 6, 7, 8 and 9% monomer solution. Then TEMED (22 μl of a 1:10 (v/v) water solution) and sodium persulfate (18 μl of a 22 mg/ml water solution) were added and the solution mixed by pipetting. The whole solution was transferred to a 4 mm diameter glass tube (washed in chromic acid) and carefully overlaid with distilled water. The gels polymerized in about 30 min and then the overlaying solution was substituted for the SDS buffer described above. The gels were left overnight at room temperature. Next day, the gels were pre-electrophoresed in the same SDS buffer for 3 hours at 50 V in Pharmacia vertical electrophoresis unit GE 2/4. The protein samples were treated with the sample buffer (1% SDS, 2% mercaptoethanol, 30% sucrose and bromphenol blue in the SDS buffer described above) for 15 min at 56° C. The proteins (from Bio-Rad) include myosin (MW 200 000), beta-galactosidase (MW 116 000), phosphorylase b (MW 97 000), bovine serum albumin (MW 67 000) and ovalbumin (MW 45 000). The samples in 5 μl were applied to the gels and run at 80 V and 18° C. for 1.5 h. The gels were then removed from the glass tubes and a piece of wire was inserted in the middle of the bromphenol blue band. Fixing of the gels was done in a water solution containing 20% ethanol and 7% acetic acid, followed by staining with 0.1% Coomassie Brillant Blue R-250 overnight in the same solution. The gels were first destained with the same water-ethanol-acetic acid solution and then with 7% acetic acid. Destaining was faster than in the poly(NAT) and polyacrylamide gels. The migration distances were measured in destained gels.

The same procedure was used to prepare 6, 8 and 10% poly(NAT) and polyacrylamide gels. The electrophoretic conditions and subsequent gel treatment was identical to that described for the poly(N-acryloyl-1-amino-1-deoxy-D-glucitol) gels.

EXAMPLE 2

SDS Electrophoresis of Proteins in poly(N-acryloyl-1-amino-1-deoxy-D-galactitol) Gels N-acryloyl-1-amino-1-deoxy-D-galactitol (0.97 g), recrystallized from water-methanol, and Bis (0.03 g) were dissolved with gentle heating to give 10 ml of the solution as described in Example 1. The gels were prepared, run and analyzed further as described in Example 1. The destaining process was faster than in the poly(NAT) and polyacrylamide gels.

EXAMPLE 3

SDS Electrophoresis of Proteins in poly(N-acryloyl-2-amino-2-deoxy-D-glucitol) Gels N-acryloyl-2-amino-2-deoxy-D-glucitol (0.97 g), recrystallized from ethanol, and Bis (0.03 g) were dissolved in the SDS buffer and the gels were prepared as described above. After electrophoresis and staining, the gels destained faster than poly(NAT) and polyacrylamide gels.

EXAMPLE 4

SDS Electrophoresis of Proteins in poly(N-acryloyl-N-methyl-1-amino-1-deoxy-D-glucitol) Gels N-acryloyl-N-methyl-1-amino-1-deoxy-D-glucitol (0.97 g), recrystallized from dioxane, and Bis (0.03 g) were dissolved in the SDS buffer to give 10 ml of the solution. Weighing of the monomer was difficult since it is very hygroscopic. The gels (6, 8 and 10%) destained faster than poly(NAT) gels. During staining and destaining the 6% gel swelled about 30% above its original size.

EXAMPLE 5

SDS Electrophoresis of Proteins in poly(N-acryloyl-N-methyl-1-amino-1-deoxy-D-galactitol) Gels N-acryloyl-N-methyl-1-amino-1-deoxy-D-galactitol (0.97 g), recrystallized from ethanol, and Bis (0.03 g) were dissolved in the SDS buffer to make a 10% solution. The gels destained slower than polyacrylamide gels, comparable to poly(NAT) gels. The lower concentration gels swelled, but significantly less than the poly(N-acryloyl-N-methyl-1-amino-1-deoxy-D-glucitol) gels.

EXAMPLE 6

Isoelectric Focusing in poly(N-acryloyl-1-amino-1-deoxy-D-glucitol) Gels

Two gels containing N-acryloyl-1-amino-1-deoxy-D-glucitol and Bis (T=5, C=3 and T=6, C=3) were polymerized in water with concentrations of TEMED and persulfate identical to those specified in Example 1. The gels were 1 mm thick, 92 mm long and 62 mm wide. They were covalently fixed during polymerization to a plastic support (Gel Bond, FMC Corporation). After two hour long polymerization, the gels were transferred to a vessel containing 2 l of distilled water and left overnight. The water was changed and after additional six hours the gels were left to dry. The T=5, C=3 gel remained essentially flat, whereas the other gel curled slightly after complete drying. The gels were reswollen with 7 ml of the 3.5–10 Ampholine (LKB) solution and used for separation of proteins by isoelectric focusing. Each gel was pre-focused at 3 W for 360 Vh and then the samples were applied. They included broad range pI markers from Pharmacia. The proteins were allowed to enter the gel for 15 min at 300 V. The focusing was continued for 2500 Vh, final voltage 1500 V. After fixing in 10% trichloracetic acid-5% sulfosalicylic acid, the gel was stained with Coomassie Brilliant Blue R-250. The proteins bands were very sharp in both gels, but the pH gradient was not linear when 1M NaOH and 1M $H_3PO_4$ were used as electrode solutions. A precipitate, which was difficult to remove afterwards, was occasionally observed on the gel surface.

EXAMPLE 7

Isoelectric Focusing in poly(N-acryloyl-N-methyl-1-amino-1-deoxy-D-galactitol) Gels Isoelectric focusing gels comprising N-acryloyl-N-methyl-1-amino-1-deoxy-D-galactitol and Bis (T=5, C=3 and T=6, C=3) were prepared as described in Example 6. After drying both gels curled much more than the corresponding N-acryloyl-1-amino-1-deoxy-D-glucitol gels. The protein bands were equally sharp but destaining of the gel required a longer time than destaining of gels of Example 6.

EXAMPLE 8

Electrophoresis of DNA Restriction Fragments in poly(N-acryloyl-N-methyl-1-amino-1-deoxy-D-galactitol) Gels Gels comprising the title monomer and Bis (T=6, C=2.0, 2.2, 2.4, 2.6, 2.8 and 3.0%) were polymerized in 20 mM Tris-acetate buffer pH 8.0, containing 0.5 mM disodium EDTA. The last two gels were slightly opaque, whereas the others were essentially transparent. The gels were 3 mm thick, 92 mm long and 62 mm wide. DNA standards included 123 and 1 kbp ladder (BRL). The gels were run at 7 V/cm and 25° C. for 2 h and 15 min in an improved electrophoresis unit (Elchrom), featuring a substantially uniform electric field, buffer circulation and cooling. The running buffer was 30 mM Tris-acetate pH 8.0 containing 0.75 mM disodium EDTA. The gels were stained with ethidium bromide (0.2 µg/ml overnight) and destained in water. There was a gradual decrease of migration rate as the degree of cross-linking increased. Better resolution in the lower molecular range was clearly observable in the gel with C=3 than in the gel with C=2%.

EXAMPLE 9

Electrophoresis of DNA Restriction Fragments in poly(N-acryloyl-1-amino-1-deoxy-D-glucitol) Gels Gels of the same dimensions and ionic composition as in Example 8, but with T=5.5 and C=2.4 and 3.0 were prepared from the title monomer and Bis. After electrophoresis under conditions specified above the 123 bp fragment migrated out of both gels. From 15 to 17 bands could be distinguished in both gels in the lane containing the 123 ladder. In the 1 kbp ladder the 506 and 516 fragments were resolved and the 5090 bp band was separated from other high molecular weight fragments.

EXAMPLE 10

Electrophoresis of DNA Restriction Fragments in a poly(N-acryloyl-N-methyl-1-amino-1-deoxy-D-glucitol) Gel A gel comprising the title monomer and Bis(T=6, C=3) was prepared and run as described in Example 8. The 123 bp fragment migrated out of this gel and more than 15 bands were visible in the 123 ladder. The 506 and 516 bp bands were resolved and the cluster representing unresolved high molecular weight bands migrated about 0.5 cm further than in the corresponding poly(N-acryloyl-N-methyl-1-amino-1-deoxy-D-galactitol) gel.

EXAMPLE 11

Electrophoresis of DNA Restriction Fragments in a poly(N-acryloyl-2-amino-2-deoxy-D-glucitol) Gel A gel containing N-acryloyl-2-amino-2-deoxy-D-glucitol and Bis(T=7, C=3) was polymerized and run as described in Example 8. However, after about 1 h, the gel began to detach from the plastic support. It was then removed from the electrophoresis apparatus and stained. The DNA bands were more diffuse than in other gels.

EXAMPLE 12

Electrophoresis of DNA Restriction Fragments in a poly(N-acryloyl-1-amino-1-deoxy-D-xylitol) Gel Since the title monomer remained as a viscous solution, its concentration was determined by drying a 2 ml aliquot on Celite in vacuo over phosphorous pentoxyde and weighing. A gel containing the monomer and Bis(T=6, C=3) was prepared and run as specified in Example 8. The 123 bp fragment was about 1.5 cm distant from the bottom of the gel and about 15 bands are visible in the ladder. In the 1 kbp ladder the 506 and 516 bp fragments are resolved. The bands are slightly more diffuse.

EXAMPLE 13

Electrophoresis of DNA Restriction Fragments in poly(N-acryloyl-N-methyl-1-amino-1-deoxy-D-galactitol) Gels at a Low Voltage Two gels (T=6, C=3 and T=5, C=3) cross-linked with Bis were run at 2 V/cm for 24 h. The samples include lambda/Hind III digest and 1 kbp ladder. In both gels all the six bands from the digest are fully resolved. In the T=5 gel, the 1018 bp fragment migrated to about 0.5 cm from the bottom of the gel and there are 10 bands distinguishable in the ladder. The bands are more diffuse in the 5% gel.

EXAMPLE 14

Electrophoresis of DNA Restriction Fragments in a poly(N-acryloyl-N-methyl-1-amino-1-deoxy-D-galacitol) Gel of Higher Concentration A gel comprising the title monomer and Bis(T=10, C=3) was polymerized in 40 mM Tris-acetate pH 80, containing 1 mM disodium EDTA. It was run as described in Example 8 for four hours. The 123 bp fragment migrated to about 2 cm from the gel bottom. In the 264 bp fragment there are two bands fully resolved. In the 1 kbp ladder the resolution in the 134 to 516 bp range is very good, but the resolution above 1 kbp is lost.

EXAMPLE 15

Electrophoresis of DNA Restriction Fragments in a poly(N-acryloyl-N-methyl-1-amino-1-deoxy-D-galactitol) Comprising Another Cross-Linker Gels were prepared (T=6, C=2 and 3) which contained piperazine-diacrylamide instead Bis. The gel with C=3 was strongly and the gel with C=2 slightly opaque. The resolution in the first one is poor and the gel was attached less strongly to the plastic support. The resolution in the second gel is better, but the bands are more diffuse than in the corresponding gel cross-linked with Bis.

EXAMPLE 16

Electrophoresis of DNA Restriction Fragments in a poly(N-acryloyl-N-methyl-1-amino-1-deoxy-D-galactitol) Comprising a Polymeric Cross-Linker A gel (T=6, C=2) comprising the title monomer and Acryl Aide was prepared by adding 1 g of the Acryl Aide solution (which is 2% according to the supplier) to 15.7 ml of the 20 mM buffered solution containing 1 g of the monomer. After polymerization the slightly turbid gel was run as described in Example 8. The 123 bp fragment was just at the bottom of the gel and at least 17 bands could be distinguished in the ladder. The cluster of high molecular weight bands from the 1 kbp ladder migrated further than in the corresponding gel cross-linked with Bis.

EXAMPLE 17

Electrophoresis of DNA Restriction Fragments in a Composite poly(N-acryloyl-N-methyl-1-amino-1-deoxy-D-galactitol)-poly(N-acryloyl-1-amino-1-deoxy-D-glucitol) Gel The gel (T=6, C=3) contained equal amount of the two title monomers and it was cross-linked Bis. The gel was prepared and run as described in Example 8 but the running time was slightly longer (2 h 30 min). The 123 bp fragment migrated out of the gel and at least 15 bands are distinguishable in the ladder.

EXAMPLE 18

Electrophoresis of DNA Restriction Fragments in a Composite poly(N-acryloyl-N-methyl-1-amino-1-deoxy-D-galactitol)-polyacrylamide Gel The gel (T=6, C=3) contained N-acryloyl-N-methyl-1-amino-1-deoxy-D-galactitol and acrylamide in equal amount. The cross-linker was Bis. The gel was prepared and run as specified in Example 8 but the running time was 2 h and 30 min. In this gel the 123 bp fragment was about 2.5 cm distant from the gel bottom and 8 bands are clearly distinguishable in the ladder. The resolution of DNA bands above 1 kbp is poor in the 1 kbp ladder.

EXAMPLE 19

Electrophoresis of DNA Restriction Fragments in a Composite poly(N-acryloyl-N-methyl-1-amino-1-deoxy-D-galactitol) Gel Cross-Linked with Two Cross-Linkers A gel (T=6, C=3) comprising the title monomer was polymerized in presence of PDA and Bis. The weight ratio of the two cross-linkers was 1:2. The gel was prepared and run as described in Example 8. It was significantly opaque and the DNA bands were more diffuse than in the corresponding gel cross-linked only with Bis. The 123 bp fragment was about 0.8 cm apart from the bottom of the gel.

EXAMPLE 20

Capillary Gel Electrophoresis of DNA Restriction Fragments

When the monomers of the present invention were prepared in capillaries under standard conditions, in most of them bubbles appeared after polymerization, as observed under a microscope. The use of 30% lower quantities of the initiator and catalyst enabled preparation of several gel-filled capillaries suitable for electrophoresis. The inside wall of the capillary was first silanized, as described in reference 19. A poly(N-acryloyl-N-methyl-1-amino-1-deoxy-D-galactitol)-Bis gel (T=6, C=2%), polymerized inside a 40 cm long capillary with an internal diameter of 100 μm, was used to separate DNA fragments present in a pBr322/Hae III digest. Running buffer was 30 mM Tris-acetate pH 8.0, containing 0.75 mM disodium EDTA. The gel was run in the Waters Quanta 4000 apparatus. The gel length to detector was 33 cm. Preelectrophoresis was conducted at 4000 V for 30 and then the samples were applied by electromigration for 10 seconds at 3 kV. The electrophoresis continued for about 30 min at 4 kV. Then the voltage was raised to 7 kV and after additional 30 min all fragments passed the detector. The result (FIG. 4) shows that all fragments were resolved, except the 123/124 bp pair.

EXAMPLE 21

Synthesis of N-acryloyl-2-amino-2-deoxy-D-glucitol.

The starting material for preparation of this monomer is N-acetyl-2-amino-2-deoxy-D-glucose. The synthesis includes mainly three steps, which are described below.

Step 1

N-acetyl-2-amino-2-deoxy-D-glucose was first reduced to the corresponding glucitol. Thus 0.5 mol (110.6 g) of N-acetyl-2-amino-2-deoxy-D-glucose was dissolved in about 400 ml water and the solution was cooled in an ice bath. Then 0.2 mol (7.6 g) of sodium borohydride was dissolved in about 50 ml of 1M sodium hydroxide. This solution was added in small portions into the efficiently stirred sugar solution. The stirring process was continued for 2-4 h after all sodium borohydride had been added. At this time, there should be an excess of unreacted sodium boronhydride, which is checked by dropping one drop of the reaction solution into 50% acetic acid. If no hydrogen bubbles are generating (visible), some more $NaBH_4$ is added to the reaction mixture. (Note 1. This may be the case with too old $NaBH_4$ preparations). If hydrogen is liberated, the reaction mixture is treated with Amberlite IR-120, H+. The resin was added carefully (to prevent excessive foaming) in small portions, whilst stirring and cooling in the ice bath was continued. About 200-300 ml of the resin was added. After additional stirring, there was usually very little sodium left, as detected by burning a drop of solution on platinum wire. The remaining sodium was remove by passing the reaction mixture through a 100 ml column filled with Dowex 50, H+ (200-400 or 100-200 mesh). The reaction mixture, which contains now N-acetyl-2-amino-2-deoxy-D-glucitol and boric acid, was evaporated under reduced pressure at 30°-40° C. The resulting syrup was mixed with about 200 ml of methanol-acetic acid solution (20:1, v/v) and evaporated. This procedure was repeated 4-5 times, and served to remove boric acid as trimethyl borate.

Step 2

The syrupy residue was dissolved in 500 ml of 2 m HCl and the solution was refluxed for 4-8 h. The solution was concentrated by evaporation and then dried in a desiccator over phosphorous pentoxide and potassium hydroxide pellets. The product, 2-amino-2-deoxy-D-glucitol hydrochloride, can be obtained in the crystalline state but this is not necessary for the next step. The yield of the crude, yellow to brownish product ranged from 73 to 89% from four different preparations.

Step 3

The crude 2-amino-2-deoxy-D-glucitol hydrochloride was dissolved in about 300 ml of water and the pH of this solution was adjusted to 8.0-8.5 with 5M KOH. Then 1-2 g of sodium nitrite and 100-150 mol of methylene chloride were added, and the solution was cooled in an ice bath. Acryloyl chloride (10% molar excess over 2-amino-2-deoxy-D-glucitol) was mixed with the same volume of methylene chloride. Potassium hydroxide, equal to twice the molar amount of acryloyl chloride, was dissolved in water and cooled. The well stirred two-base reaction mixture, portions of acryloyl chloride and KOH solutions were added in such a way that the pH remained between 7.5.-9.5 (as checked frequently by a narrow range pH paper). After the last additions of acryloyl chloride and KOH solutions, the reaction mixture was further stirred for about one hour (the pH was periodically checked and corrected, if necessary). The two phases were allowed to separate in a separating funnel and the lower organic phase was discarded. The aqueous phase was treated in one of two ways. A fraction of salts was precipitated with addition of four volumes of absolute ethanol and then the remaining salts were bound to the mixed ion exchangers. Alternatively, the precipitation step was omitted and the salts were directly removed by mixed ion exchangers. To the stirred solution, portions of Amberlite IR-120 H+ and IRA-68 (free base) were added (pH being kept neutral or slightly acid) until the silver reaction for chloride was negative. The resin was then removed, the filtrate treated with activated charcoal and the solution poured into crystallization dishes. A small quantity (several hundred mg) of p-methoxy phenol (polymerization inhibitor) was added. The solvents evaporated within 1-2 weeks. The monomer appeared as a hard, slightly yellow but almost transparent residue. The yield ranged from 43-56% with regard to the starting materials, N-acetyl-2-amino-2-deoxy-D-glucose. The produce was pulverized and recrystallized from ethanol, m.p. 133-135 (polymerization).

Note 2

An attempt was done to prepare the same compound by reacting 2-amino-2-deoxy-D-glucose and acryloyl chloride, followed by reduction of the product with sodium boronhydride. However, it was not possible to get pure N-acryloyl-2-amino-2-deoxy-D-glucitol in this way.

EXAMPLE 22

Synthesis of N-acryloyl-N-methyl-1-amino-1-deoxy-D-glucitol

N-methyl-1-amino-1-deoxy-D-glucitol (0.5 mol, 97.6 g) was dissolved in about 300 ml of water. Then 1-2 g of sodium nitrite was added and the solution was cooled in an ice bath. Potassium hydroxide (0.6 mole) was dissolved in water and cooled. Acryloyl chloride (0.55 mole) was mixed with an equal volume of methylene chloride. The reaction was done in the same way as described in step 3 for the synthesis of N-acryloyl-2-amino-2-deoxy-D-glucitol. The salts were also removed as described above. However, even after several weeks long evaporation from a crystallization dish, the product was not dry. After addition of more polymerization inhibitor, drying was continued in a desiccator. The semi-dry mass (yield 41–60%) was dissolved in warm dioxane which contained p-methoxy phenol. The warm solution was filtered through Celite and upon cooling the crystals were formed. They were collected and recrystallized from dioxane. The title compound is very hygroscopic.

EXAMPLE 23

Synthesis of N-methacryloyl-N-methyl-1-amino-1-deoxy-D-glucitol

This compound was prepared in two slightly different ways. The first way was identical to the preparation of N-acryloyl-N-methyl-1-amino-1-deoxy-D-glucitol described above. In contrast to the previous one, this monomer readily crystallized upon drying in crystallization dishes (yield 62–80%). It was recrystallized from ethanol, m.p. 142–144.

A simpler way involved the use of lithium hydroxide instead of potassium hydroxide to neutralize hydrochloride acid that was formed during the reaction. After separation of the two phases, the water phase was without any treatment poured into crystallization dishes. After a few days in a fume cupboard, the title compound crystallized from a highly concentrated salt (mostly LiCl) solution. The crystals were collected and washed with ethanol. The yield was lower (about 50%).

EXAMPLE 24

Polymerization of N-acryloyl-2-amino-2-deoxy-D-glucitol

The monomer (450 mg) was dissolved in water to give 4.5% (w/v) solution (10 ml). To this solution were added μl of 50% (v/v) N,N,N'-tetramethylethylenediamine (TEMED) solution, followed by 155 μl of ammonium persulfate solution (15 mg/ml). The monomer solution was overlaid by diisopropyl ether. After 24 h at room temperature a highly viscous solution was produced. The polymerization of N-acryloyl-2-amino-2-deoxy-D-glucitol at high concentration (above 10%, w/v) in water usually resulted in extremely viscous polymers and/or gels that were not completely soluble in water.

EXAMPLE 25

Isoelectric Focusing of Proteins in a poly-N-acryloyl-2-amino-2-deoxy-D-glucitol-Bis Gel The gel (T=7, C=3) was polymerized on a plastic sheet (Gel Bond), which contained polymerization double bonds. In this way the gel was covalently linked to the plastic support. After polymerization the gel was washed three times with distilled water. It was then air-dried overnight at room temperature. The broad range (3.5–10) carrier ampholytes were introduced into the gel by the overlay technique, and the pre-focusing was done for 500 Vh. The standard proteins were applied to the gel, which was run for 2600 Vh. The following standard proteins can be seen after Coomassie Brilliant Blue staining (FIG. 3): 1, trypsinogen (pI 9.3); lentil lectin basic band (pI 8.65); 3, lentil lectin middle band (pI 8.45); 4, lentil lectin acidic band (pI 8.15); 5, myoglobin basic band (pI 7.35); 6, myoglobin acidic band (pI 6.85); 7, human carbonic anhydrase (pI 6.55); 8, bovine carbonic anhydrase (pI 5.85); 9,beta-lactoglobulin A (pI 5.2); 10, soybean trypsin inhibitor (pI 4.55); 11, amyloglucosidase (pI 3.50).

EXAMPLE 26

Figure 4:
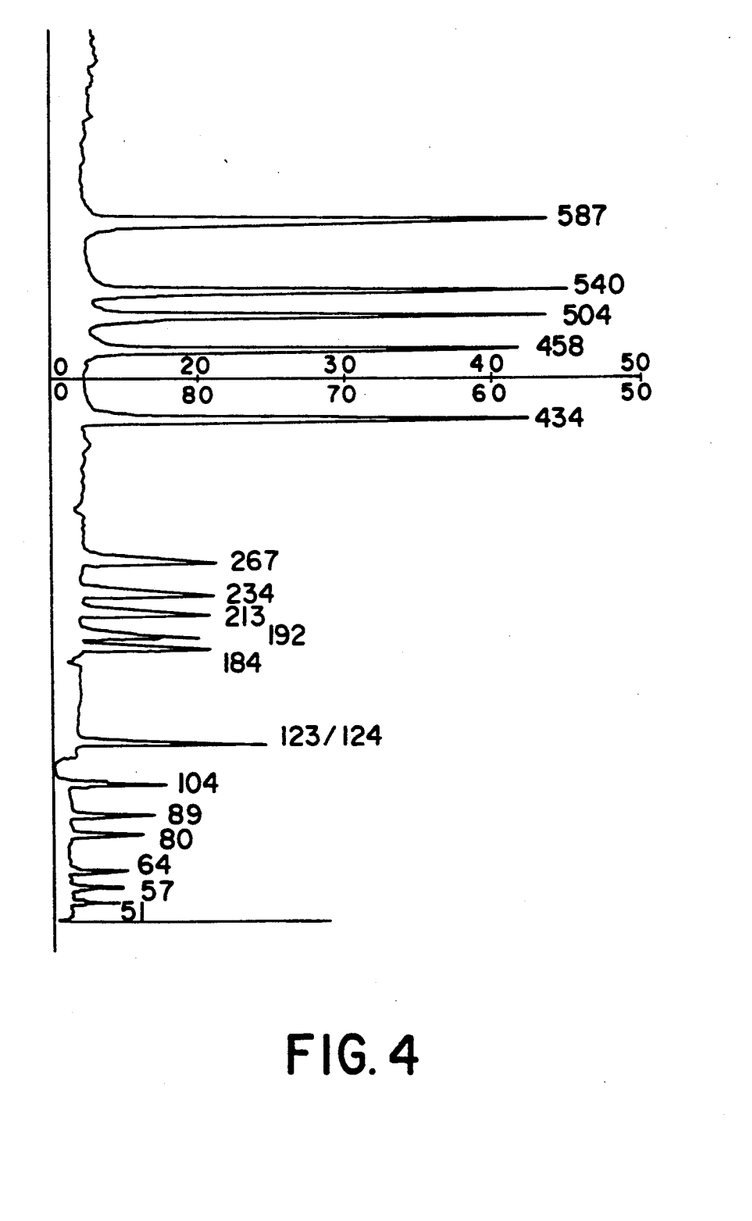
FIG. 4 shows separation of DNA fragments present in a pBr322/Hae III digest separated by capillary gel electrophoresis. The fragment size (in base pairs) is marked above the corresponding peak.

Preparation of an Opaque poly-N-acryloyl-2-amino-2-deoxy-D-glucitol-Bis Gel in the Form of Beads A solution (4 ml) was prepared which contained the title monomer and the cross-linker (T=15, C=12), as well as 85 mg of poly-vinylalcohol (mW 15,000). Then, 24 ml of diethyl succinate containing 13 mg of Span 20 was deaerated (degassed), with magnetic stirring under high vacuum. This solution was then transferred into an apparatus designed for suspension polymerization (Arshady, R., and Ledwith, A. (1983) Reactive Polymers, 31 2, 2 159–174). The stirrer was inserted and a stream of nitrogen was continuously passed through the apparatus. After about 30 min, 18 μl of TEMED and 230 μl of ammonium persulfate (15 mg/ml) were added to the monomer solution, which was quickly, by means of a syringe, transferred into the apparatus. The suspension was stirred vigorously for about one hour. The formed beads were removed by gentle filtration and then washed with water by decantation. FIG. 4 shows the beads prepared in this way.

EXAMPLE 27

Synthesis of N-acryloyl-N-ethyl-1-amino-1-deoxy-D-galacitol

The N-ethyl-1-amino-1-deoxy-D-galacitol (63 g) is mixed with about 300 ml of water and 1 g of sodium nitrite. Then 100–150 ml of methylene chloride are added, and the solution is cooled in an ice bath. Acryloyl chloride (10% molar excess over the amine) is mixed with the same volume of methylene chloride. Potassium hydroxide, equal to twice the molar amount of acryloyl chloride, is dissolved in water and cooled. To the well stirred two-phase reaction mixture, portions of acryloyl chloride and KOH solutions were added in such a way that the pH remained between 7.5–9.5 (as checked frequently by a narrow range pH paper). After the last additions of acryloyl chloride and KOH solutions, the reaction mixture was further stirred for about one hour (the pH was periodically checked and corrected, if necessary). The two phases were allowed to separate in a separating funnel and the lower organic phase was discarded. The aqueous phase was treated with charcoal and filtered. The filtrate was treated with a combination of ion exchangers either in solution or by passing the filtrate through columns packed with ion exchangers. Thus, to the stirred solution, portions of Amberlite IR-120,H+ and IRA-68 (free base) were added (pH being kept neutral or slightly acid) until the silver reaction for chloride was negative. The resin was then removed, the filtrate treated with activated charcoal and the solution poured into crystallization dishes. Alternatively, the monomer solution was passed through 600 ml of IR-120 and 600 ml of IRA-68, preferentially packed in more than two columns. The solution passed always first through the cationic ion exchanger. A small quantity (several hundred mg) of p-methoxy phenol or sodium nitrite (polymerization inhibitors) were added to the monomer solution. The water evaporated within 1-2 weeks. The monomer appeared as a white solid. The yield was 72%. The monomer was recrystallized from ethanol-acetone, m.p. 80°-84° C. (polymerization).

EXAMPLE 28

Synthesis of N-acryloyl-N-propyl-1-amino-1-deoxy-D-galacitol

The synthesis was carried out substantially as described in Example 27. The yield was 75%. The monomer was recrystallized from ethanol-acetone, m.p. 128°-130° C. (polymerization).

EXAMPLE 29

Synthesis of N-acryloyl-N-butyl-1-amino-1-deoxy-D-galacitol

The synthesis was carried out substantially as described in Example 27. The yield was 66%. The monomer was recrystallized from acetonitrile, m.p. 120°-123° C. (polymerization).

The corresponding glucitol derivative remained as a viscous aqueous solution.

EXAMPLE 30

Synthesis of N-acryloyl-N-hexyl-1-amino-1-deoxy-D-glucitol

The amine was suspended in water and mostly converted into its hydrochloride salt by addition of hydrochloric acid. The synthesis was then done essentially as described in Example 27, except that the amount of KOH needed was higher. The yield was 76%. The monomer was recrystallized from acetonitrile, m.p. 86°-88° C. (polymerization).

EXAMPLE 31

Synthesis of N-acryloyl-N-octyl-1-amino-1-deoxy-D-glucitol

The starting amine was first converted into its hydrochloride salt as described in Example 30. The synthesis was then carried out as described in Example 27. However, a larger portion of UV positive material was found in the methylene chloride than in the water phase. After evaporation of methylene chloride a slightly yellow solid mass was obtained. The crystallization attempts failed.

EXAMPLE 32

Synthesis of N-acryloyl-N-phenylethyl-1-amine-1-deoxy-D-galacitol

The starting amine was first converted mostly into its hydrochloride salt and the synthesis was then continued as described in Example 27. The yield was 37%. The monomer crystallized after evaporation of water, m.p. 52°-56° C.

EXAMPLE 33

Synthesis of N-acryloyl-N-(2-hydroxyethyl)-1-amino-1-deoxy-D-galacitol

The synthesis was done as described in Example 27. After evaporation of water the monomer appeared as a semi-solid white material. It was recrystallized from ethanol. The crystals were filtered and washed with acetone. A large portion of solvent remained within the monomer. When evaporation of the remaining solvent was tried in the air, the monomer liquified but became semi-solid again after several days. After drying in vacuo over phosphorous pentoxide, the monomer was obtained as a hard solid. It is hygroscopic.

The corresponding glucitol derivative remained as a viscous aqueous solution. When stored refrigerated as 40% solution, after several months a fungi-like semi-solid, almost transparent material appeared and grew to the size of over 3 cm.

EXAMPLE 34

Synthesis of N-acryloyl-amino-N,N,-bis(1 deoxy-D-galacitol)

The synthesis was done essentially as described in Example 27. Due to lower water solubility the amine was partially converted into its hydrochloride salt. The monomer crystallized after evaporation of water. The yield was 62%. The monomer is hardly soluble in methanol or ethanol and the crystallization attempts failed. The melting point was greatly dependent on the heating rate, being much higher (above 130° C.) at a slow rate.

The corresponding glucitol derivative remained as an aqueous solution.

EXAMPLE 35

Preparation of a Water Soluble Polymer from N-acryloyl-N-ethyl-1-amino-1-deoxy-D-galacitol The monomer (0.3 g) and sorbitol (0.75 g) were dissolved in water and diluted to 5 ml in a glass test tube. The TEMED (12 μl) and ammonium persulfate (150 μl of a 15 mg/ml water solution) were added. The solution was overlaid with diisopropylether and polymerized overnight at room temperature. A viscous polymer solution was obtained.

EXAMPLE 36

Preparation of Water Soluble and Insoluble Copolymers from acrylamide and N-acryloyl-N-hexyl-1-amino-1-deoxy-D-glucitol Different amounts of monomers were dissolved in 50 mM Tris-HCl buffer pH 8.8 to give total monomer concentration 0.43, 0.7, 1.0, 1.29 and 1.57M and ratios of acrylamide to the N-hexyl monomer of 7:1, 5:1 and 3:1. The solutions (300 μl) were polymerized in microtiter plates. Polymerization was started by adding to the 0.43M solution 4 μl of TEMED and 5.9 μl of ammonium persulfate (AP, 15 mg/ml), to the 0.7M solution 3.9 μl of TEMED and 5.7 μl of AP, to the 1M solution 3.8 μl of TEMED and 5.5 μl of AP, to the 1.29M solution 3.7 μl of TEMED and 5.4 μl of AP and to the 1.57M solution 3.6 μl of TEMED and 5.3 μl of AP. Some solutions remained transparent whereas in others a precipitate was formed. In FIG. 5, soluble polymers are shown as white, not dotted, circles, precipitated polymers as dotted circles, stronger dotted for more precipitated polymers. The solubility clearly depends on the total monomer concentration as well as the molar ratio of acrylamide to the amphiphatic monomer.

A 10 ml solution of acrylamide and N-acryloyl-N-hexyl-1-amino-1-deoxy-D-glucitol containing 4% (w/v) total monomer and 7:1 molar ratio of acrylamide to N-hexyl monomer was polymerized with 10 μl of TEMED and 120 μl of ammonium persulfate (15 mg/ml). There resulted a viscous solution which foamed after agitation.

EXAMPLE 37

Preparation of Water Soluble and Insoluble Copolymers from N-acryloyl-1-amino-1-deoxy-D-glucitol and N-acryloyl-N-hexyl-1-amino-1-deoxy-D-glucitol Twelve solutions were prepared by having different molar ratios and total concentrations of monomers as described in Example 36. After polymerization, the same TEMED and AP concentrations were used in Example 36. Most combinations gave polymers which did not form visible precipitates. This is in contrast with copolymers comprising acrylamide instead of N-acryloyl-1-amino-1-deoxy-D-glucitol, demonstrating that copolymers with a higher amount of hydrophobic residues remain water soluble by increasing the hydrophilicity of the hydrophilic monomer.

A 5 ml water solution of N-acryloyl-1-amino-1-deoxy-D-glucitol and N-acryloyl-N-hexyl-1-amino-1-deoxy-D-glucitol containing 0.75 g sorbitol and 6% (w/v) total monomer with 10:1 molar ratio of the hydrophilic to amphiphatic monomer was polymerized by addition of 8 μl TEMED and 100 μl ammonium persulfate (15 mg/ml). There resulted a viscous solution foamed upon agitation.

When the total monomer concentration was increased to 9% (w/v) or above, it was not possible to obtain polymers which completely dissolved after dilution with water.

EXAMPLE 38

Transparent and Opaque Gels from acrylamide, N-acryloyl-N-hexyl-1-amino-1-deoxy-D-glucitol and N,N'-methylene-bis-acrylamide Fifteen solutions were polymers which contained form 0.43 to 1.57M total monomer concentration and molar ratios of acrylamide to the N-hexyl monomer from 3:1 to 7:1. The same amount of TEMED and AP as described in Example 36 were added. Each solution contained the same percentage of the cross-linker (C=1%, w/w) in relation to the total monomer. The opacity of gels is dependent on the total monomer concentration as well as the ration of acrylamide and the amphiphatic monomer.

EXAMPLE 39

Transparent and Opaque Gels from N-acryloyl-1-amino-1-deoxy-D-glucitol, N-acryloyl-N-hexyl-1-amino-1-deoxy-D-glucitol and N,N'-methylene-bis-acrylamide Twelve solutions were polymerized which contained from 0.43 to 1.29M total monomer and from 3:1 to 7:1 molar ratio of the hydrophilic to the amphiphatic monomer. Each solution had the same percentage of the cross-linker (C=1%, w/w) in relation to the total monomer. Most combinations yielded transparent gels. That is different to the result obtained with acrylamide (Example 38), where most combinations yielded slightly to fully opaque gels.

EXAMPLE 40

A Transparent Gel from N-acryloyl-N-butyl-1-amino-1-deoxy-D-galacitol and 1,2-dihydroxyethylene-bis-acrylamide To a 5 ml water solution of the monomers (T=8%, C=3%) in a glass test tube TEMED (9 μl) and ammonium persulfate (100 μl, 15 mg/ml solution) were added. After two hours a transparent gel was formed.

EXAMPLE 41

Electrophoresis in the Gel Prepared from N-acryloyl-N-(2-hydroxyethyl)-1-amino-1-deoxy-D-glucitol and N,N'-methylene-bis-acrylamide As described in Example 33, this monomer was obtained as a concentrated water solution. That solution was treated with a mixture of ion exchangers (containing a blue indicator, from Bio Rad) and then with activated charcoal. The solution was first filtered through a filter paper and then through a nitrocellulose membrane filter (0.45 μm). The concentration of the monomer solution was estimated by measuring the absorbance at 260 nm of the appropriately diluted sample and comparing it to the standard curve obtained with crystalline N-acryloyl-N-methyl-1-amino-1-deoxy-D-galacitol.

The concentrated solution was 40% (w/v). A part of it was diluted to give a 7% solution in 30 mM Tris-acetate buffer pH 8.4, containing 2 mM ethylenediaminetetraacetic acid. In 20 ml of this solution N,N'-methylene-bis-acrylamide (42 mg) was dissolved to give C=3%. Then TEMED (23 μl) and ammonium persulfate (270 μl, 15 mg/ml) were added and the gel polymerized in a plastic cassette (7×10 cm), having sample well formers about 5 mm apart from edge of the shorter side. The gel was approximately 3 mm thick and the sample wells were about 3 mm deep and 5 mm long. The gel was polymerized on a plastic support (PAGE GelBond, FMC). After 4 hours at room temperature, the cassette was opened and the gel placed in an electrophoretic apparatus for submerged gel electrophoresis. The apparatus (home made) was equipped with a pump for buffer circulation and the gel rested on a cooling plate. Three different DNA standard mixtures were applied to the gel. They included 1 kbp ladder (from BRL), 123 bp ladder (from BRL and lambda/Hind III fragments (from Biofinex). The gel was run at 20° C. in 30 mM Tris-acetate buffer pH 8.4, containing 2 mM EDTA at 4 V/cm for 4 hours. Then it was stained with ethidium bromide (1 μg/ml) and distained with water. DNA bands were visualized under UV light. All DNA fragments migrated further than in the poly(NAT-Bis) gel (T=7%, C=3) which was run as a control, demonstrating a larger effective pore size. In the 1 kbp ladder, 506 and 516 DNA bands were clearly resolved as were 3 and 4 kbp bands. In the 123 bp ladder, at least 12 bands well resolved. In the lambda/Hind III mixture, the 2.0 and 2.2 kbp fragments were well resolved.

EXAMPLE 42

Electrophoresis in the Gel Prepared from N-acryloyl-amino-N,N'-bis(1-deoxy-D-galacitol) and N,N'-methylene-bis-acrylamide The monomer (1.6 g) and the cross-linker (48 mg) were dissolved in 10 ml of water and the solution treated with mixed ion exchanger and charcoal as described in Example 41. The filtered solution was diluted to 20 ml with 60 mM Tris-acetate pH 8.4, containing 4 mM EDTA. The gel was then polymerized, run and stained as described in Example 41. All DNA fragments migrated much further than in the corresponding poly(-NAT-Bis) gel and somewhat further than the gel of Example 41. The bands were slightly broader than in the gel of Example 41. In the 1 kbp ladder 506 and 516 DNA bands were resolved and in 123 bp ladder at least 10 bands were clearly visible.

EXAMPLE 43

Electrophoresis in the Gel Prepared from N-acryloyl-N-ethyl-1-amino-1-deoxy-D-galacitol and N,N'-methylene-bis-acrylamide The gel (T=6%, C=3%) solution was prepared by dissolving the monomer and cross-linker in the running buffer. The solution was polymerized to a perfectly transparent gel, which was run for 3 h at 4 V/cm and stained as described in Example 41. The bromphenol blue migrated slightly ahead of 123 bp fragment. In the 1 kbp ladder, 506 and 516 bp bands were resolved and the distances between upper bands were slightly larger than in the corresponding N-acryloyl-N-methyl-1-amino-1-deoxy-D-galacitol gel run as a control at the same time. In the 123 bp ladder, at least 13 bands were distinguishable. In the lambda/Hind III fragments, 2.0 and 2.2 kbp bands were resolved. After electrophoresis the gel was somewhat swollen (thicker) and swelling becomes more pronounced during staining and destaining. Such swelling was not noticed with other gels examined. Once the gel detached from the supporting plastic.

EXAMPLE 44

Electrophoresis in the Gel Prepared from N-acryloyl-N-propyl-1-amino-1-deoxy-D-galacitol and N,N'-methylene-bis-acrylamide The gel was prepared and run essentially as described in Example 43. The gel was very slightly opaque, which was noticeable when looking through the long side of the gel. The DNA bands were somewhat sharper and better resolved than in the gel of Example 43, although the migration distances were comparable. Bromphenol blue migrated in this gel approximately as the 246 bp fragment. The 506 and 516 bp bands were well resolved and at least 13 bands were distinguishable in the 123 bp ladder. The 2.0 and 2.2 kbp bands were also well resolved.

EXAMPLE 45

Electrophoresis in the Gel Prepared from N-acryloyl-N-butyl-1-amino-1-deoxy-D-galacitol and N,N'-methylene-bis-acrylamide The gel was prepared and run essentially as described in Example 43. This gel was considerably more opaque than the gel of Example 44. The DNA fragments migrated a similar distance but the bands were generally broader. The 506 and 516 bp were distinguishable and the 2.0 and 2.2 kbp were resolved, although not so well as in other gels. Bromphenol blue concentrated as it entered the gel and it also changed the color (to paler blue). At the end of the run bromphenol blue migrated approximately the same distance as the 1 kbp band from the 1 kbp ladder. This gel was mechanically weaker than the previous two gels and had a tendency to detach from the plastic support.

EXAMPLE 46

Electrophoresis in the Gels Prepared from N-acryloyl-N-hexyl-1-amino-1-deoxy-D-glucitol, acrylamide and N,N'-methylene-bis-acrylamide in the Presence of 0.02% SDS The gels (T=12%, C=1%) contained various molar ratios of acrylamide and the N-hexyl monomer. The gel was polymerized in 0.375M Tris-HCl pH 8.8 containing 0.02% SDS in glass tubes (inner diameter 4 mm, lengthy 7 cm). A stacking gel (T=4%, C=1%) was polymerized in 0.125M Tris-HCL pH 6.8. The running buffer was 50 mM Tris-0.384M glycine buffer pH 8.3. Bovine serum albumin heated in the stacking gel buffer containing 1% SDS and 3% mercaptoethanol and applied to the gel. The gels were run until bromphenol blue in the control gel reached the bottom of the gel. Proteins were detected by Coomassie Brilliant Blue R-250 staining. The migration of BSA was found to be dependent on the ratio of acrylamide and the N-hexyl monomer, slightly decreasing in the gels with higher amounts of the amphiphatic monomer. The first gel was polymerized without N-acryloyl-N-hexyl-1-amino-1-deoxy-D-glucitol (1-NHAGU), the last one with N-acryloyl-1-amino-1-deoxy-D-glucitol (1-NAGA, 20:1 molar ratio).

EXAMPLE 47

Electrophoresis in the Gels Prepared from N-acryloyl-N-hexyl-1-amino-1-deoxy-D-glucitol, acrylamide and N,N'-methylene-bis-acrylamide in the Presence of 0.05% SDS The gels were prepared and run as described in Example 46. At this higher concentration of SDS the protein was retarded even in the gel with 160:1 molar ratio of acrylamide to the N-hexyl monomer. BSA migrated only very little in the gel with the 20:1 ratio.

EXAMPLE 48

Electrophoresis in the Gels Prepared from N-acryloyl-N-hexyl-1-amino-1-deoxy-D-glucitol, acrylamide and N,N'-methylene-bis-acrylamide in the Presence of 0.1% SDS The gels were prepared and run as described in Example 46. The 90:1 gel BSA migrated approximately half the distance it migrated in the gel without 1-NHAGU (first gel) and it hardly entered the 20:1 gel.

EXAMPLE 49

Electrophoresis in the Gels Prepared from N-acryloyl-N-hexyl-1-amino-1-deoxy-D-glucitol, acrylamide and N,N'-methylene-bis-acrylamide in the Presence of 0.2% SDS The gels were prepared and run as described in Example 46. The 160:1 gel BSA migrated less than half the distance it migrated in the gel without 1-NHAGU (first gel). The protein remained on the top of 40:1 and 20:1 gels.

REFERENCES

1. Kozulic, M., Kozulic, B., and Mosbach, K. (1987) Anal. Biochem. 163, 506–512
2. Kozulic, B., Mosbach, K., and Pietrzak., M. (1988) Anal. Biochem. 170, 478–484
3. Kozulic, B., and Mosbach, K. U.S. patent application Ser. No. 07/328,123
4. Artoni, G., Gianazza, E., Zanoni, M., Gelfi, C., Tanzi, M.C., Barozzi C., Ferruti, P., and Righetti, P. G. (1984) Anal. Biochem. 137, 420–428
5. Whistler, R. L., Panzer, H. P., and Roberts, J. (1961) J. Org. Chem. 26, 1583–1588
6. Klein, J., and Herzog, D. (1987) Macromol. Chem. 188, 1217–1232
7. Kozulic. B. (1989) U.S. patent application Ser. No. 293,840
8. Hansson, H. A., and Kagedal, S. L. U.S. Pat. No. 4,312,739
9. Cook, R. B., and Witt, H. J. U.S. Pat. No. 4,290,911
10. Rodbard, D., and Chrambach, A. (1970) Proc. Natl. Acad. Sci. 65, 970–977
11. Tietz, D. in Advances in Electrophoresis, (1988) Chrambach, A., Dunn, M. J. and Radola, B. J. Editors, VCH Verlag
12. Poduslo, J. F., and Rodbard, D. (1980) Anal. Biochem. 101, 394–406
13. Neville, D. M. Jr. (1971) J. Biol. Chem. 246, 6328–6334
14. Gulseley, K. B. U.S. Pat. No. 3,956,273
15. Righetti, P. G. (1983) in Isoelectric Focusing: Theory, Methodology and Applications, Elsevier Biomedical Press, pp 160–165
16. Kozulic, B. UK Patent Application 9104411.5
17. Kozulic, B., and Heimgartner, U., UK Patent Application 9024428.6
18. Pino, R. M., and Hart, T. K. (1984) Anal. Biochem. 139, 77–81
19. Horowitz, P. M., Lee, J. C., Williams, G. A., Williams, R. F. and Barnes, L. D. (1984) Anal. Biochem. 143, 333–340

I claim:

1. A method of separating molecules which comprises subjecting such molecules to electrophoresis while in effective contact with a separation medium comprising a polymer comprising a monomer of the formula:

$$\begin{array}{c} R_1 \quad R_2 \quad R_3 \\ | \quad | \quad | \\ HC-N-C-C=CH_2 \\ | \quad \| \\ (HCOH)_n \quad O \\ | \\ CH_2OH \end{array}$$

wherein $R_1$ is H, $CH_2OH$ or $(CHOH)_mCH_2OH$, m being 1 or 2;

$R_2$ is hydrogen, monohydroxyalkyl, polyhydroxyalkyl, or hydrocarbon radical;

$R_3$ is H or $CH_3$; and n is an integer of 1–4;

migrating ionic species of said molecules in said medium thereby separating said species from each other.

2. A method as claimed in claim 1, wherein said separation medium comprises an aqueous cross-linked gel comprising a polymer comprising a monomer of the formula:

$$\begin{array}{c} R_1 \quad R_2 \quad R_3 \\ | \quad | \quad | \\ HC-N-C-C=CH_2 \\ | \quad \| \\ (HCOH)_n \quad O \\ | \\ CH_2OH \end{array}$$

wherein $R_1$ is H, $CH_2OH$ or $(CHOH)_mCH_2OH$, m being 1 or 2;

$R_2$ is H or $CH_3$;

$R_3$ is H or $CH_3$; and n is an integer of 1–4;

and a cross-linker with at least two polymerizable double bonds.

3. A method of claim 2, wherein the said gel is polymerized in a mold and used in that mold for electrophoretic separation.

4. A method of claim 3, wherein the gel is in form of a rod.

5. A method of claim 3, wherein the gel is in form of a sheet.

6. A method of claim 3, wherein the gel is in form of a thin filament.

7. A method of claim 2, wherein the said gel is in form of a sheet grafted onto a solid support.

8. A method of claim 7, wherein the solid support is a plastic material.

9. A method of claim 7, wherein the solid support is glass.

10. A method of one of claims 1 or 2, wherein the ionic species comprise polypeptides.

11. A method of one of claims 1 or 2, wherein the ionic species comprise polynucleotides.

12. A method of one of claims 1 or 2, wherein the ionic species have molecular weight below 1000.

13. A method as claimed in one of claims 1 or 2 including the further step of detecting said separated species.

14. A method of one of claims 1 or 2, including detection of said separated species by interaction with a specific stain.

15. A method of one of claims 1 or 2, including transferring said separated species to another material and thence detecting said separating species.

16. A method of one of claims 1 or 2, including providing a detector fixed in relation to said gel, and detecting said separated species by interaction with said detector.

17. A method of one of claims 1 or 2, including detecting said separated species by interaction with a scanning detector.

18. A method as claimed in claim 1 wherein said $R_2$ contains 1–30 carbon atoms.

* * * * *